United States Patent [19]

Crowl et al.

[11] Patent Number: 4,925,784
[45] Date of Patent: May 15, 1990

[54] EXPRESSION AND PURIFICATION OF AN HTLV-III GAG/ENV GENE PROTEIN

[75] Inventors: Robert M. Crowl, Cedar Grove; Daru Young, Verona, both of N.J.

[73] Assignee: Hoffmann-La Roche Inc., Nutley, N.J.

[21] Appl. No.: 848,671

[22] Filed: Apr. 4, 1986

[51] Int. Cl.$^5$ .......................................... G01N 33/569
[52] U.S. Cl. .......................................... 435/5; 530/350; 530/387; 530/395; 530/402; 530/403; 530/825; 530/826; 530/812; 435/7; 436/811
[58] Field of Search .................. 435/5, 7; 422/61; 530/300, 324, 350, 387, 395, 402, 403, 825, 826, 812; 436/811

[56] References Cited

U.S. PATENT DOCUMENTS

| | | | |
|---|---|---|---|
| 4,237,224 | 12/1980 | Cohen et al. | 435/68 |
| 4,304,863 | 12/1981 | Collins et al. | 435/172 |
| 4,751,180 | 6/1988 | Cousens et al. | 435/68 |
| 4,753,873 | 6/1988 | Beltz et al. | 435/5 |

FOREIGN PATENT DOCUMENTS

| | | | |
|---|---|---|---|
| 181107 | 5/1986 | European Pat. Off. | 435/5 |
| 181150 | 5/1986 | European Pat. Off. | 435/5 |
| 187041 | 7/1986 | European Pat. Off. | 435/5 |
| 199301 | 10/1986 | European Pat. Off. | 435/5 |
| 199438 | 10/1986 | European Pat. Off. | 435/5 |
| 213894 | 3/1987 | European Pat. Off. | 435/5 |
| 214555 | 3/1987 | European Pat. Off. | 435/5 |
| 214709 | 3/1987 | European Pat. Off. | 435/5 |
| 219106 | 4/1987 | European Pat. Off. | 435/5 |
| 230222 | 7/1987 | European Pat. Off. | 435/5 |
| 233044 | 8/1987 | European Pat. Off. | 435/5 |
| 85/04903 | 11/1985 | World Int. Prop. O. | 435/5 |
| 86/00930 | 2/1986 | World Int. Prop. O. | 435/5 |
| 86/01535 | 3/1986 | World Int. Prop. O. | 435/5 |
| 86/01827 | 3/1986 | World Int. Prop. O. | 435/5 |
| 86/06099 | 10/1986 | World Int. Prop. O. | 435/5 |
| 86/06414 | 11/1986 | World Int. Prop. O. | 435/5 |
| 87/02038 | 4/1987 | World Int. Prop. O. | 435/5 |
| 87/02775 | 5/1987 | World Int. Prop. O. | 435/5 |
| 87/05399 | 9/1987 | World Int. Prop. O. | 435/5 |

OTHER PUBLICATIONS

Schupbach et al., Science 224:503 (1984).
Shaw et al., Science 226:1165 (1984).
Crowl et al., Gene 38:31 (1985).
Dowbenko et al., Proc. Natl. Acad. Sci. U.S.A. 82:7748 (1985).
Sarngadharan et al., Science 224:506 (1984).
Casadaban et al., J. Mol. Biol. 138:179 (1980).
Chang et al., Biotechnology 3:905 (1985).
Crowl et al., Cell 41:979 (1985).
Grayeb et al., DNA 5:93 (1986).
Kiyokawa et al., Proc. Natl. Acad. Sci. U.S.A. 81:6202 (1984).
Steimer et al., Virology 150:283 (1986).
Sugano, JP 60-166624A, in: Patents Abstracts of Japan, Section C, vol. 10 (1986), No. 13, (C-323).
Westhoff, Suddentsche Zeitung, Feb. 10, 1984, p. 18.
Yoshida, JP 60-166699A, in: Patents Abstracts of Japan, Section C, vol. 10 (1986), No. 13, (C-323).
Yoshida, JP 60-190799A, in: Patents Abstracts of Japan, Section C, vol. 10 (1986), No. 43, (C-329).

(List continued on next page.)

*Primary Examiner*—Christine M. Nucker
*Attorney, Agent, or Firm*—George M. Gould; William H. Epstein

[57] ABSTRACT

Methods and compositions are provided for the cloning and expression of plasmids bearing genes encoding a novel protein derived from HTLV-III. This protein, which is called the gag/env protein and which contains antigenic determinants from both the core and envelope proteins of HTLV-III, can be purified to homogeneity and used as the basis for diagnostic tests to detect the presence of antibodies against viruses associated with AIDS or the viruses themselves in human sera and other biological fluids. The gag/env protein may also be formulated for use as a vaccine for protection against AIDS through prophylactic immunization.

6 Claims, 3 Drawing Sheets

OTHER PUBLICATIONS

Chang, et al., "Expression in *Escherichia coli* of Open Reading Frame Gene Segments of HTLV-III", Science, 228 (1985) 93–96.

Ratner et al., "Complete nucleotide sequence of the AIDS Virus, HTLV-III", Nature, 313 (1985) 277–284.

Wain-Hobson et al., "Nucleotide Sequence of the AIDS Virus, LAV", Cell, 40 (1985) 9–17.

Meusing et al., "Nucleic Acid Structure and Expression of the Human AIDS Lymphadenopathy Retrovirus", Nature, 313 (1985) 450–458.

Dowbenko et al., "Bacterial Expression of the Acquired Immunodeficiency Retrovirus p24 gag Protein and its Use as a Diagnostic Reagent", Proc. Nat'l. Acad. Sci. U.S.A., 82 (1985) 7748–7752.

Sarngadharan et al., "Immunological Properties of HTLV-III Antigens Recognized by Sera of Patients with AIDS and AIDS-related Complex and of Asymptomatic Carriers of HTLV-III Infection", Can. Res., 45 (1985) 4574s–4577s.

Chang et al., "Detection of Antibodies to Human T-Cell Lymphotropic Virus-III (HTLV-III) with an Immunoassay Employing a Recombinant *Escherichia coli*-Derived Viral Antigenic Peptide", Bio/Technology, 3 (1985) 905–909.

Shoeman et al., "Comparison of Recombinant Human Immunodeficiency Virus gag Precursor and gag/env Fusion Proteins and a Synthetic env Peptide as Diagnostic Reagents", Anal. Biochem., 161 (1987) 370–379.

FIGURE 1

```
                                    ClaI
ATG AAT AGA ATT CGG ATC CAT CGA TGG GAA AAA ATT CGG TTA AGG CCA GGG GGA
MET Asn Arg Ile Arg Ile His Arg Trp Glu Lys Ile Arg Leu Arg Pro Gly Gly
                             15  gag--->

AAG AAA AAA TAT AAA TTA AAA CAT ATA GTA TGG GCA AGC AGG GAG CTA GAA CGA
Lys Lys Lys Tyr Lys Leu Lys His Ile Val Trp Ala Ser Arg Glu Leu Glu Arg

TTC GCA GTT AAT CCT GGC CTG TTA GAA ACA TCA GAA GGC TGT AGA CAA ATA CTG
Phe Ala Val Asn Pro Gly Leu Leu Glu Thr Ser Glu Gly Cys Arg Gln Ile Leu

GGA CAG CTA CAA CCA TCC CTT CAG ACA GGA TCA GAA GAA CTT AGA TCA TTA TAT
Gly Gln Leu Gln Pro Ser Leu Gln Thr Gly Ser Glu Glu Leu Arg Ser Leu Tyr

AAT ACA GTA GCA ACC CTC TAT TGT GTG CAT CAA AGG ATA GAG ATA AAA GAC ACC
Asn Thr Val Ala Thr Leu Tyr Cys Val His Gln Arg Ile Glu Ile Lys Asp Thr

AAG GAA GCT TTA GAC AAG ATA GAG GAA GAG CAA AAC AAA AGT AAG AAA AAA GCA
Lys Glu Ala Leu Asp Lys Ile Glu Glu Glu Gln Asn Lys Ser Lys Lys Lys Ala

CAG CAA GCA GCA GCT GAC ACA GGA CAC AGC AGT CAG GTC AGC CAA AAT TAC CCT
Gln Gln Ala Ala Ala Asp Thr Gly His Ser Ser Gln Val Ser Gln Asn Tyr Pro

ATA GTG CAG AAC ATC CAG GGG CAA ATG GTA CAT CAG GCC ATA TCA CCT AGA ACT
Ile Val Gln Asn Ile Gln Gly Gln MET Val His Gln Ala Ile Ser Pro Arg Thr

TTA AAT GCA TGG GTA AAA GTA GTA GAA GAG AAG GCT TTC AGC CCA GAA GTA ATA
Leu Asn Ala Trp Val Lys Val Val Glu Glu Lys Ala Phe Ser Pro Glu Val Ile

CCC ATG TTT TCA GCA TTA TCA GAA GGA GCC ACC CCA CAA GAT TTA AAC ACC ATG
Pro MET Phe Ser Ala Leu Ser Glu Gly Ala Thr Pro Gln Asp Leu Asn Thr MET

CTA AAC ACA GTG GGG GGA CAT CAA GCA GCC ATG CAA ATG TTA AAA GAG ACC ATC
Leu Asn Thr Val Gly Gly His Gln Ala Ala MET Gln MET Leu Lys Glu Thr Ile

AAT GAG GAA GCT GCA GAA TGG GAT AGA GTA CAT CCA GTG CAT GCA GGG CCT ATT
Asn Glu Glu Ala Ala Glu Trp Asp Arg Val His Pro Val His Ala Gly Pro Ile

GCA CCA GGC CAG ATG AGA GAA CCA AGG GGA AGT GAC ATA GCA GGA ACT ACT AGT
Ala Pro Gly Gln MET Arg Glu Pro Arg Gly Ser Asp Ile Ala Gly Thr Thr Ser

ACC CTT CAG GAA CAA ATA GGA TGG ATG ACA AAT AAT CCA CCT ATC CCA GTA GGA
Thr Leu Gln Glu Gln Ile Gly Trp MET Thr Asn Asn Pro Pro Ile Pro Val Gly
```

Figure 2

```
GAA ATT TAT AAA AGA TGG ATA ATC CTG GGA TTA AAT AAA ATA GTA AGA ATG TAT
Glu Ile Tyr Lys Arg Trp Ile Ile Leu Gly Leu Asn Lys Ile Val Arg MET Tyr

AGC CCT ACC AGC ATT CTG GAC ATA AGA CAA GGA CCA AAA GAA CCT TTT AGA GAC
Ser Pro Thr Ser Ile Leu Asp Ile Arg Gln Gly Pro Lys Glu Pro Phe Arg Asp

TAT GTA GAC CGG TTC TAT AAA ACT CTA AGA GCC GAG CAA GCT TCA CAG GAG GTA
Tyr Val Asp Arg Phe Tyr Lys Thr Leu Arg Ala Glu Gln Ala Ser Gln Glu Val

AAA AAT TGG ATG ACA GAA ACC TTG TTG GTC CAA AAT GCG AAC CCA GAT TGT AAG
Lys Asn Trp MET Thr Glu Thr Leu Leu Val Gln Asn Ala Asn Pro Asp Cys Lys

ACT ATT TTA AAA GCA TTG GGA CCA GCG GCT ACA CTA GAA GAA ATG ATG ACA GCA
Thr Ile Leu Lys Ala Leu Gly Pro Ala Ala Thr Leu Glu Glu MET MET Thr Ala

TGT CAG GGA GTA GGA GGA CCC GGC CAT AAG GCA AGA GTT TTG GCT GAA GCA ATG
Cys Gln Gly Val Gly Gly Pro Gly His Lys Ala Arg Val Leu Ala Glu Ala MET

AGC CAA GTA ACA AAT ACA GCT ACC ATA ATG ATG CAG AGA GGC AAT TTT AGG AAC
Ser Gln Val Thr Asn Thr Ala Thr Ile MET MET Gln Arg Gly Asn Phe Arg Asn

CAA AGA AAG ATG GTT AAG TGT TTC AAT TGT GGC AAA GAA GGG CAC ACA GCC AGA
Gln Arg Lys MET Val Lys Cys Phe Asn Cys Gly Lys Glu Gly His Thr Ala Arg

AAT TGC AGG GCC CCT AGG AAA AAG GGC TGT TGG AAA TGT GGA AAG GAA GGA CAC
Asn Cys Arg Ala Pro Arg Lys Lys Gly Cys Trp Lys Cys Gly Lys Glu Gly His
                                                        BglII
CAA ATG AAA GAT TGT ACT GAG AGA CAG GCT AAT TTT TTA GGG AAG ATC TTC AGA
Gln MET Lys Asp Cys Thr Glu Arg Gln Ala Asn Phe Leu Gly Lys Ile Phe Arg
                                                  <---gag 436/467 env--->
CCT GGA GGA GGA GAT ATG AGG GAC AAT TGG AGA AGT GAA TTA TAT AAA TAT AAA
Pro Gly Gly Gly Asp MET Arg Asp Asn Trp Arg Ser Glu Leu Tyr Lys Tyr Lys GTA GTA AAA ATT GAA CCA TTA GGA GTA GCA CCC ACC AAG GCA AAG AGA AGA GTG
Val Val Lys Ile Glu Pro Leu Gly Val Ala Pro Thr Lys Ala Lys Arg Arg Val GTG CAG AGA GAA AAA AGA GCA GTG GCA GCA GGA AGC ACT ATG GGC GCA GCG TCA
Val Gln Arg Glu Lys Arg Ala Val Ala Ala Gly Ser Thr MET Gly Ala Ala Ser ATG ACG CTG ACG GTA CAG GCC AGA CAA TTA TTG TCT GGT ATA GTG CAG CAG CAG
MET Thr Leu Thr Val Gln Ala Arg Gln Leu Leu Ser Gly Ile Val Gln Gln Gln AAC AAT TTG CTG AGG GCT ATT GAG GCG CAA CAG CAT CTG TTG CAA CTC ACA GTC
Asn Asn Leu Leu Arg Ala Ile Glu Ala Gln Gln His Leu Leu Gln Leu Thr Val
```

Figure 2 continued

```
TGG GGC ATC AAG CAG CTC CAG GCA AGA ATC CTG GCT GTG GAA AGA TAC CTA AAG
Trp Gly Ile Lys Gln Leu Gln Ala Arg Ile Leu Ala Val Glu Arg Tyr Leu Lys

GAT CAA CAG CTC CTG GGG ATT TGG GGT TGC TCT GGA AAA CTA CTT TGC ACC ACT
Asp Gln Gln Leu Leu Gly Ile Trp Gly Cys Ser Gly Lys Leu Leu Cys Thr Thr

GCT GTG CCT TGG AAT GCT AGT TGG AGT AAT AAA TCT CTG GAA CAG ATT TGG AAT
Ala Val Pro Trp Asn Ala Ser Trp Ser Asn Lys Ser Leu Glu Gln Ile Trp Asn

HindIII
CAC ACG ACG TGG ATG GAG TGG GAC AGA GAA ATT AAC AAT TAC ACA AGC TTT AAT
His Thr Thr Trp MET Glu Trp Asp Arg Glu Ile Asn Asn Tyr Thr Ser Phe Asn
                                                              640

GCG GTA GTT TAT CAC AGT TAA
Ala Val Val Tyr His Ser  .
```

EXPRESSION AND PURIFICATION OF AN HTLV-III GAG/ENV GENE PROTEIN

TABLE OF CONTENTS

1. Field of the Invention
2. Background of the Invention
   2.1. Etiology of Aids
   2.2. Recombinant DNA Technology
3. Summary of the Invention
4. Brief Description of the Figures
5. Description of the Invention
   5.1. Identification and Isolation of the gag and env Genes
   5.2. Cloning and Expression of the gag/env Protein Gene
   5.3. Isolation of the gag/env Protein
   5.4. Use of the gag/env Protein and Antibodies Against the Protein
      5.4.1. Detection of Antibodies Against AIDS Viruses
      5.4.2. Detection of AIDS Viruses or Viral Particles
      5.4.3. Immunization Against AIDS
6. Example
   6.1. General Procedures for Recombinant Vector Preparation
      6.1.1. DNA Preparation
      6.1.2. Conditions for Enzymatic Reactions
      6.1.3. Purification of DNA Fragments in Agarose
      6.1.4. Culture Media
      6.1.5. Transformation and Isolation of Recombinants
      6.1.6. Cell Growth and Induction of Gene Expression
      6.1.7. SDS Polyacrylamide Gel Electrophoresis and Western Blot Analysis
      6.1.8. Primer-Directed Mutagenesis
      6.1.9. Colony Hybridizations
   6.2. Construction of Plasmid pEV2/gag 15–512
   6.3. Construction of Plasmid pEV3/env 44–640 Δ319–331
   6.4. Construction of Plasmid pEV3/env 44–640 Δ319–331 Δ514–524
   6.5. Construction of Plasmid pEV2/gag 15–436/env 467–640 Δ514–524

1. FIELD OF THE INVENTION

The present invention relates to a protein designated gag/env, which comprises the core protein (gag) and the envelope protein (env) of the HTLV-III virus, the etiologic agent for acquired immune deficiency syndrome (AIDS). This protein is produced through organic synthetic methods or through the use of recombinant DNA techniques in which the requisite gene sequences are inserted by means of a suitable DNA vector into a compatible unicellular host organism.

This invention further relates to the isolation and purification of the gag/env protein and to methods for the detection of AIDS antibodies or viruses in human sera or other biological fluids and for the immunoprophylactic protection of human beings against AIDS, based on the use of the protein.

2. BACKGROUND OF THE INVENTION

2.1. ETIOLOGY OF AIDS

In 1985 nearly 8,000 people were diagnosed as having AIDS, and the number has been steadily increasing. Fifteen thousand more cases are expected to be diagnosed in 1986, and the number of cases may well double again in 1987. New York Times Magazine, Mar. 2, 1986, p. 42. AIDS has been characterized by the onset of severe opportunistic infections secondary to an effect on the body's immune system. Gottlieb et al., New Eng. J. Med. 305:1426 (1981). The disease has been found in male homosexuals, patients receiving blood products, intravenous drug addicts and individuals originating from Haiti and Central Africa. Piot et al., Lancet 11:65 (1984).

The causative agent was suspected to be of viral origin because the epidemiological pattern of AIDS was consistent with that of a transmissible disease. At least three retroviruses have been isolated from cultured T-cells of several patients with AIDS, or from white blood cells of persons at risk for the disease. A novel human retrovirus called lymphadenopathy-associated virus (LAV) was discovered, and its properties were consistent with an etiological role in AIDS. That virus was isolated from a patient with lymphadenopathy and hence the name. Montagnier et al., in Human T-Cell Leukemia/Lymphoma Virus, R. C. Gallo et al. eds., Cold Spring Harbor Laboratory, pp. 363–370 (1984).

Other human retroviruses, specifically two subgroups of the human T-cell leukemia/lymphoma/lymphotropic virus, types I [Poicsz et al., Proc. Natl. Acad. Sci. U.S.A. 77:7415 (1980)] and III [Popovic et al., Science 224:797 (1984)] have also been isolated. Still another virus, called the AIDS-associated retrovirus (ARV), has been proposed as the causative agent [Levy et al., Science 225:840 (1984)]. Both the HTLV-III and ARV retroviruses display biological and seroepidemiological properties similar to LAV. Levy et al., supra, Popovic et al., supra. Thus, at least three retroviruses have been postulated to be the etiologic agent or AIDS: LAV, ARV, and HTLV-III. For this application, these viruses will be collectively referred to as the AIDS viruses. Because HTLV-III is the prototypic virus for this group, it will be understood that the term "antigenic determinant corresponding to the sequences of a protein of an HTLV-III virus" actually refers to the sequences of the proteins of any of the AIDS viruses.

One reason for the difficulty in determining the true etiologic agent of AIDS was cross-reactivity of various retroviral antigens with serum samples from AIDS patients. For example, serum samples from AIDS patients have been shown to react with antigens of both HTLV-I [Essex et al., Science 220:859 (1983)] and HTLV-III [Sarngadharan et al., Science 224:506 (1984)]. Envelope gene products of HTLV demonstrated antigenicities that were cross-reactive with antibodies in sera from adult T-cell leukemia patients. Kiyokana et al., Proc. Natl. Acad. Sci. U.S.A. 81:6202 (1984). Adult T-cell leukemias (ATL) differ from acquired immune deficiency syndrome (AIDS) in that HTLV-I causes T-cell malignancies that are characterized by the uncontrolled growth of T-cells. In AIDS, instead of cell growth there is cell death. In fact this cytopathic characteristic of HTLV-III was critical to ultimately determining the specific retroviral origin of the disease.

The etiologic agent of AIDS was isolated by the use of immortalized human neoplastic T cell lines (HT) infected with the cytopathic retrovirus characteristic of AIDS, isolated from AIDS afflicted patients. Seroepidemiological assays using this virus showed a complete correlation between AIDS and the presence of antibodies to HTLV-III viral antigens. Gallo et al., supra, 1984; Sarngadharan et al., supra, 1984; Schupbach et al., Science 224:503 (1984). In addition, nearly 85% of patients with lymphadenopathy syndrome and a significant proportion of asymptomatic homosexual men in AIDS endemic areas were also found to carry circulating antibodies to HTLV-III. Taken together, these data implicate HTLV-III as the principal etiologic agent for AIDS.

Until the successful culturing of the AIDS virus using the H-9 cell line, the env AIDS protein of the AIDS virus had not been isolated, characterized or synthesized. This in major part was due to the fact that the virus is cytopathic, and isolation of the virus was thus not possible. Popovic et al., Science 224:497 (1984). Once a human T-cell line that was resistant to the cytopathic effects of the virus was discovered, however, the molecular cloning of AIDS proviral DNA could be carried out.

The need for sensitive and rapid methods for the diagnosis of AIDS in human blood and in other biological fluids and for a method to prevent the disease by vaccination is very great. Virtually all of the assays and tests presently available are fraught with errors. In fact, the Center for Disease Control (CDC) has indicated that presently available tests should be used solely for screening units of blood for the presence of antibodies to HTLV-III. The CDC has even gone further by stating that the presently available enzyme-linked immunosorbent assay (ELISA) tests should not be used for the general screening of high risk populations or as a diagnostic test for AIDS. Federal Register 50(48):9909, Mar. 12, 1985.

The errors in previously used AIDS tests have been traced to the failure to use a specific antigenic protein of the etiologic agent for AIDS. The previously used proteins were derived from a viral lysate. Since the lysate is made from human cells infected with the virus, i.e. the cells used to grow the virus, the lysate will contain human proteins as well as viral proteins. Thus preparation of a pure antigen of viral protein is very difficult. The antigens used until now have thus produced both false positive and false negative results. Budiansky, Nature 312:583 (1984). The errors caused by the use of such lysate proteins/peptides could be avoided by using a composition for binding AIDS antibodies which is substantially free of the non-AIDS specific proteins. Compositions of substantially pure AIDS envelope and core protein can be used as antigens.

Both the envelope and core proteins of HTLV-III have conserved antigenic determinants which would permit their use to screen for, diagnose and/or provide protection by vaccination against the AIDS viruses. And individuals that have been exposed to HTLV-III and who may thus be at risk to contract AIDS or who have the disease can be identified by the presence in their blood of antibodies to the viral core protein (gag) and/or the envelope protein (env). Sarngadharan et al., Science 224:506 (1984).

The availability of a reliable and sensitive test for the presence in blood or in other biological fluids of the AIDS virus itself, or of particles therefrom, is also important. Groopman et al. [Blood 66:742 (1985)] have reported that antibodies against AIDS viruses are not always present in the blood of AIDS victims. Groopman et al. examined one patient with AIDS and another with related disorders (ARC) from whom blood samples were taken which were antibody negative but from which HTLV-III could be cultured.

2.2. RECOMBINANT DNA TECHNOLOGY

In the application of current recombinant DNA procedures, specific DNA sequences are inserted into an appropriate DNA vehicle, or vector, to form recombinant DNA molecules that can replicate in host cells. Circular double-stranded DNA molecules called plasmids are frequently used as vectors, and the preparation of such recombinant DNA forms entails the use of restriction endonuclease enzymes that can cleave DNA at specific base sequence sites. Once cuts have been made by a restriction enzyme in a plasmid and in the segment of foreign DNA that is to be inserted, the two DNA molecules may be covalently linked by an enzyme known as a ligase. General methods for the preparation of such recombinant DNA molecules have been described by Cohen et al. [U.S. Pat. No. 4,237,224], Collins et al. [U.S. Pat. No. 4,304,863] and Maniatis et al. [Molecular Cloning: A Laboratory Manual, 1982, Cold Spring Harbor Laboratory]. Because they illustrate much of the state of the art, these references are hereby incorporated by reference.

Once prepared, recombinant DNA molecules can be used to produce the product specified by the inserted gene sequence only if a number of conditions are met. Foremost is the requirement that the recombinant molecule be compatible with, and thus capable of autonomous replication in, the host cell. Much recent work has utilized *Escherichia coli* (*E. coli*) as a host organism because it is compatible with a wide range of recombinant plasmids. Depending upon the vector/host cell system used, the recombinant DNA molecule is introduced into the host by transformation, transduction or transfection.

Detection of the presence of recombinant plasmids in host cells may be conveniently achieved through the use of plasmid marker activities, such as antibiotic resistance. Thus, a host bearing a plasmid coding for the production of an ampicillin-degrading enzyme could be selected from unaltered cells by growing the host in a medium containing ampicillin. Further advantage may be taken of antibiotic resistance markers where a plasmid codes for a second antibiotic-degrading activity at a site where the selected restriction endonuclease makes its cut and the foreign gene sequence is inserted. Host cells containing properly recombinant plasmids will then be characterized by resistance to the first antibiotic but sensitivity to the second.

The mere insertion of a recombinant plasmid into a host cell and the isolation of the modified host will not in itself assure that significant amounts of the desired gene product will be produced. For this to occur, the foreign gene sequence must be fused in proper relationship to a signal region in the plasmid for DNA transcription called a promoter. Alternatively, the foreign DNA may carry with it its own promoter, as long as it is recognized by the host. Whatever its origin, the promoter is a DNA sequence that directs the binding of RNA polymerase and therefore "promotes" the transcription of DNA to messenger RNA (mRNA).

Given strong promotion that can provide large quantities of mRNA, the ultimate production of the desired gene product will be dependent upon the effectiveness of translation from mRNA to protein. This, in turn, is dependent upon the efficiency of ribosomal binding to the mRNA. In *E. coli*, the ribosome-binding site on mRNA includes an initiation codon (AUG) and an upstream Shine-Dalgarno (SD) sequence. This sequence, containing 3-9 nucleotides and located 3-11 nucleotides from the AUG codon, is complementary to the 3' end of E. coli 16S ribosomal RNA (rRNA) [Shine and Dalgarno, Nature 254:34 (1975)]. Apparently, ribosomal binding to mRNA is facilitated by base pairing between the SD sequence in the mRNA and the sequence at the 16S rRNA 3' end. For a review on maximizing gene expression, see Roberts and Lauer, Methods in Enzymology 68:473 (1979).

Recombinant DNA technology has recently been applied to the AIDS problem. The molecular cloning and expression of the env gene from HTLV-III has been reported by Crowl et al., Cell 41:979 (1985) and by Chang et al., Biotechnology 3:905 (1985). Dowbenko et al., Proc. Natl. Acad. Sci. U.S.A. 82:7748 (1985) have expressed the HTLV-III core protein in E. coli.

Through the use of such genetic engineering techniques, purified viral antigens that are safe, reliable and less costly to produce have become available. Even more advantageous, however, would be the availability of a viral protein having antigenic determinants that are present on both the env and the gag proteins. Such a protein would be an exceptionally powerful tool for the detection of AIDS antibodies, and it could serve as the basis for a variety of sensitive diagnostic tests and for a possible vaccine against the AIDS virus.

3. SUMMARY OF THE INVENTION

Methods and compositions are provided for the cloning and expression in single-cell host organisms of genes coding for a novel protein having at least one antigenic determinant corresponding to the sequences of a gag and env protein of an HTLV-III virus. Methods are also described for the preparation and culturing of the modified host organisms to produce the gag/env protein and for the isolation and purification of this product. The gag/env protein thus produced may be utilized by the methods of this invention for a number of important immunological processes.

Through use as a diagnostic reagent, the gag/env protein can be used to detect the presence in human serum of antibodies against AIDS viruses. Because the protein can be prepared in a homogeneous form, problems of non-specific reactions which have plagued the use of diagnostic reagents based upon relatively crude HTLV-III viral protein isolates in the past are eliminated.

Used as an immunogen, the gag/env protein can be employed to produce antibodies in animals against the antigenic determinants contained therein. Such antibodies can in turn be used, in conjunction with the gag/env protein which has been suitably labeled, in a radioimmunoassay (RIA) or enzyme-linked immunosorbent assay (ELISA) to detect the presence of HTLV-III viruses or particles therefrom in human serum or in other biological fluids.

By incorporation into a suitable vaccine formulation, the gag/env protein of the invention may further be used to combat the spread of AIDS through prophylactic immunization.

4. BRIEF DESCRIPTION OF THE FIGURES

The present invention may be more readily understood by reference to the following figures, wherein

FIG. 3 shows the results of SDS-polyacrylamide gel electrophoretic analysis of the gag/env protein produced in E. coli. Panel 1 shows Coomassie blue-stained total cell proteins from cells harboring the recombiant plasmid carrying the gag/env fusion gene and from control cells. Panels 2 and 3 are Western blots of total cell protein probed with either rabbit antibodies against env peptide 500-511 (panel 2) or sheep antibodies against gag p24 (panel 3). The immune complexes in panels 2 and 3 were visualized by a second antibody labeled with horseradish peroxidase. In all three panels g/e refers to the gag/env protein, and c refers to a negative control sample used to show specificity. The mobilities of molecular weight standards (in kD) are shown, and the position of the gag/env protein band in the gels is indicated by the arrows.

5. DESCRIPTION OF THE INVENTION

This invention relates to the use of gene splicing methodology to produce a novel protein comprising substantial portions of the core (gag) and evelope (env) proteins of HTLV-III. This invention further relates to the use of the purified gag/env protein as the basis for diagnostic tests to detect the presence of antibodies against HTLV-III or the virus itself (or fragments therefrom) in human sera or in other biological fluids such as tears, semen, vaginal secretions and saliva. Fragments (or particles) that could be detected by the methods of this invention of course include pieces of the viral core or envelope proteins. This invention still further relates to the use of the gag/env protein in vaccine formulations for possible protection against AIDS by prophylactic immunization.

There are important advantages to using the gag/env protein of the invention, compared to using searate gag and env proteins. The env protein itself is very insoluble, which makes purification difficult. Combination of the two proteins results in a product that is more easily solublized and therefore more easily purified. Large-scale production and purification are also simplified, of cource, when only a single molecule must be isolated. Finally, the gag/env protein makes possible the development of a diagnostic kit which works better in an antigen sandwich assay than would separate gag and env proteins.

Although the gag/env protein was derived from HTLV-III, it must be understood that the diagnostic and immunoprophylactic methods described herein are applicable to the detection of any of the other viral agents which have been implicated in or associated with AIDS such as lymphadenopathy-associated virus (LAV) and AIDS-associated retrovirus (ARV). This is because Crowl et al. [Cell 41: 979 (1985)] have shown that proteins from these viral agents are immunologically related to those of HTLV-III and have amino acid sequence segments to common.

The methods of this invention entail a number of steps which, in logical sequence, include (1) identification and isolation of the genes encoding the gag and env proteins or fragments thereof, (2) insertion of these genes or gene fragments into an appropriate cloning vehicle to produce a recombinant vector containing a gag/env fusion gene, (3) transfer of the recombinant cloning vehicle into a compatible single cell host organism, (4) selection and growth of properly modified hosts that can replicate and express the inserted gene sequences, (5) identification and purification of the gene product, (6) use of the gene product to detect antibodies against HTLV-III or related viruses or an as immunogen to produce antibodies that can in turn be used to detect the viruses themselves or fragments therefrom in human sera or in other biological fluids, and (7) use of the gag/env protein in a vaccine formulation for possible immunoprophylactic protection against AIDS.

5.1. IDENTIFICATION AND ISOLATION OF THE GAG AND ENV GENES

Isolated HTLV-III virions could be used as the source for both the gag and the env genes of the invention. For example, Dowbenko et al. [Proc. Natl. Acad. Sci. U.S.A. 82:7748 (1985) have used a 2.2 kilobase (kb) fragment from the 5' region of the viral genome as a source of the gag gene. Alternatively, genomic DNA from cells into which the proviral genome of HTLV-III has been integrated can be the gene source [Shaw et al., Science 226:1165 (1984)]. Crowl et al. [Cell 41:979 (1985)] have used such genomic DNA from H9 cells infected with HTLV-III to obtain the env gene.

Alternatives to the isolation of the gag and env genes include but are not limited to the chemical synthesis of the gene sequences and the preparation of DNA that is complementary to the messenger RNA produced from the genes.

Regardless of its source, DNA encoding the gag and env proteins can be cloned into bacteria, and clones containing the gag or env genes can be identified by methods that are well known in the art. For example, complimentary DNA (cDNA) probes could be prepared for the genes and used to detect clones bearing the genes through hybridization techniques.

In a preferred embodiment of the invention, a genomic library constructed by XbaI digestion of the DNA of the HTLV-III-infected H9 cells described above was cloned using a phage λ vector, and clones bearing the HTLV-III proviral genome were identified by hybridization with HTLV-III cDNA. One such clone was designated λHXB-3, and a 1700 base-pair fragment encoding most of the gag precursor protein was isolated by ClaI/HincII digestion of the DNA from this clone.

The immediate source of env gene sequenes used in the preferred embodiment of the invention was a derivative of plasmid pEV3/env 44-640 that has env codons corresponding to residues 514-524 delated (see Sections 6.4, below). This deletion surprisingly results in a significant increase in the expression of the env gene. Env sequences containing codons 467 to 640 were obtained by the BglII/HindIII cleavage of plasmid pEV3/env 44-640.

5.2. CLONING AND EXPRESSION OF THE GAG/ENV PROTEIN GENE

Once identified and isolated, the gag and env genes of HTLV-III are inserted into an appropriate expression vehicle which contains the elements necessary for transcription and translation of the inserted gene sequences. Useful clonging vehicles may consist of segments of chromosomal, nonchromosomal and synethetic DNA sequences such as various known bacterial plasmids, phage DNA, combinations of plasmids and phage DNAs such as plasmids which have been modified to employ phage DNA or other expression control sequences, or yeast plasmids. Specific cloning vehicles which could be used include but are not limited to the pEV-vrf plasmids (pEV-vrf1,-2 and -3), SV40, adenovirus, yeast, lambda gt-WES-lambda B, Charon 4A and 28, lambda-ft-1-lambda B, M13-derived vectors such as pUC8, 9, 18 and 19, pBR313, 322 and 325, pAC105, pVA51, pACY177, pKH47, pACYC184, pUB110, pMB9, ColE1, pSC101, pML21, RSF2124, pCR1 or RP4.

The insertion of the gag and env genes into a cloning vector is easily accomplished when both the genes and the desired cloning vehicle have been cut with the same restriction enzyme or enzymes, since complementary DNA termini are thereby produced. If this cannot be accomplished, it may be necessary to modify the cut ends that are produced by digesting back single-stranded DNA to produce blunt ends, or by achieving the same result by filling in the single-stranded termini with an appropriate DNA polymerase. In this way, blunt-end ligation with an enzyme such as T4 DNA ligase may be carried out. Alternatively, any site desired may be produced by ligating nucleotide sequences (linkers) onto the DNA termini. Such linkers may comprise specific oligonucleotide sequences that encode restriction site recognition sequences. The cleaved vector and the gag and env gene fragments may also be modified by homopolymeric tailing, as described by Morrow [Methods in Enzymology 68:3 (1979)].

Once either the gag or env gene or a fragment thereof has been inserted into an appropriate cloning vehicle, the other gene or gene fragment can be introduced into the vehicle by judicious restriction endonuclease cleavage to place the second gene or gene fragment into juxtaposition with the first, thereby creating a fusion gene. Of course if the gag and env genes are chemically synthesized, the fusion gene could be directly produced and introduced as a single DNA fragment into the cloning vehicle.

Figure 1:
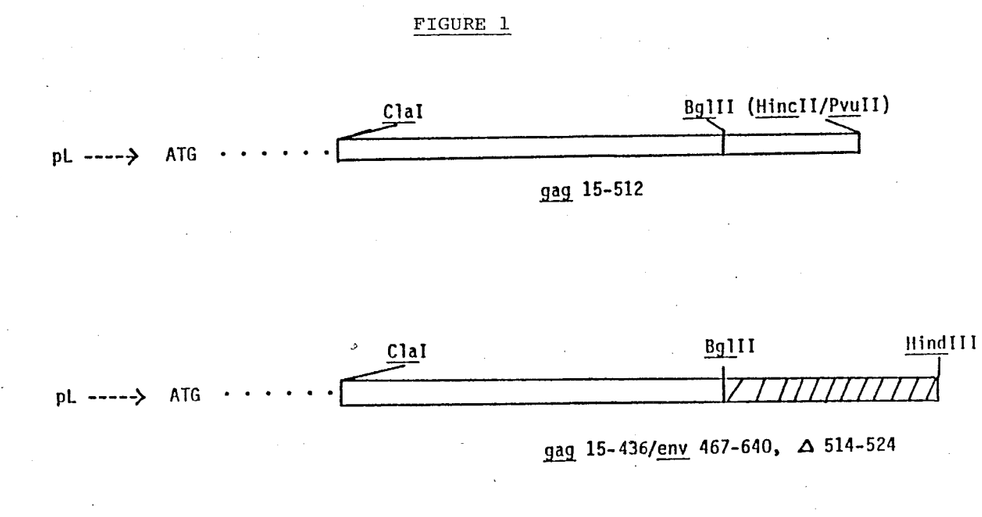
FIG. 1 is a schematic representation of expression plasmids which direct the synthesis of gag (upper drawing) and gag/env (lower drawing) proteins. Restriction endonuclease sites delineating the gag and env genes are shown, and the cross-hatched region denotes the env segment of the gag/env fusion gene. In both plasmids transcription is under the control of the λ $P_L$ promoter, and translation initiation signals are from plasmid pEV-vrf2.

In the preferred embodiment of the present invention, the ClaI/HincII digestion framgnet containing the gag gene from λHXB-3 described above was ligated into plasmid pEV-vrf2 which had been cleaved with ClaI and PuvII to produce a recombinant expression plasmid pEV2/gag 15-512 (FIG. 1, upper drawing) that directed the synthesis of a 56 Kd protein comprising gag residues 15-512. The gag sequences downstream of a BglII site near residue 437 were then replaced with env sequences in a BglII/HindIII fragment from the derivative of plasmid pEV3/env 44-640 (having residues 514-524 deleted) described above to produce plasmid pEV2/gag 15-436/env 467-640 Δ 514-524 bearing the gag/env fusion gene (FIG. 1, lower drawing).

Figure 2:
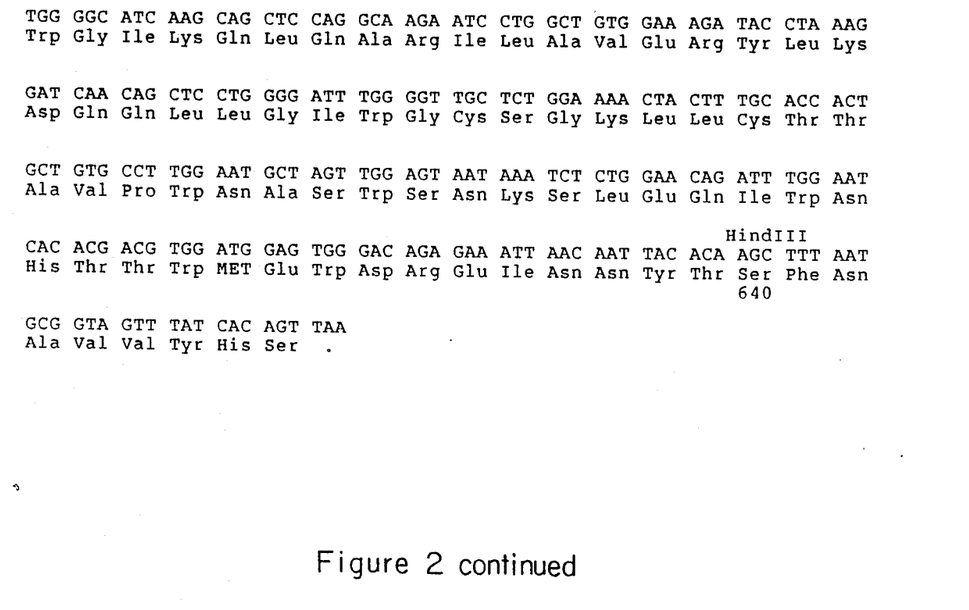
FIG. 2 shows the nucleic acid sequence of the gag/env fusion gene (with selected position numbers and restriction endonuclease sites indicated) and the amino acid sequence of the gag/env protein predicted therefrom.

Full details of this construction are provided in Sections 6.2 to 6.5. The nucleic acid sequence of the gag/env gene of the preferred embodiment [determined by the chemical cleavage method of Maxam et al., Methods in Enzymology 65:499 (1980)] and the amino acid sequence of the gag/env protein predicted therefrom are shown in FIG. 2.

Many of the cloning vehicles that may be used in this invention contain one or more marker activites that may be used to select for desired transformants, such as ampicillin and tetracycline resistance in pBR322, ampicillin resistance and β-galactosidase activity in pUC8, and ampicillin resistance in pEV-vrf2. Selection of host cells into which such vectors have been inserted is greatly simplified when the host cells otherwise lack the activities contributed by the vectors.

It should be understood that the nucleotide sequences of the gag and env gene fragments inserted at a selected site in a cloning vehicle may include nucleotides which are not part of the actual structural genes. Alternatively, the gene fragments may contain only part of the complete genes. All that is required is that the gene fragments inserted into the cloning vehicle be capable of directing the production in an appropriate host organism of a polypeptide or protein having at least one antigenic determinant corresponding to the sequences of the gag and env proteins.

The selection of an appropriate host organism is affected by a number of factors known in the art. These factors include, for example, compatibility with the chosen vector, toxicity of proteins encoded by the hybrid plasmid, ease of recovery of the desired protein, expression characteristics, biosafety and costs. A balance of these factors must be struck, and it must be understood that no all hosts will be equally effective for expression of a particular recombinant DNA molecule.

Suitable host unicellular organisms which can be used in this invention include but are not limited to plant, mammalian or yeast cells and bacteria such as *Escherichia coli, Bacillus subtilis, Bacillus stearothermophilus* and *Actinomyces*. *Escherichia coli* strain MC1061, which has been described by Casadaban et al. [J. Mol. Biol. 138:179 (1980)], can be used as can as any other strain of E. coli K-12 containing the plasmid pRK248cIts. Plasmid pRK248cIts for use in other *E. coli* K-12 strains is available from the American Type Culture Collection and has accession No. ATCC 33766. *E. coli* strain MC1061 has also been deposited and has accession No. ATCC 53338.

Transfer of the recombinant cloning vector into the host cell may be carries out in a variety of ways. Depending upon the particular vector/host cell system chosen, such transfer may be effected by transformation, transduction or transfection. Once such a modified host cell is produced, the cell can be cultured and the protein expression product may be isolated from the culture.

5.3. ISOLATION OF THE GAG/ENV PROTEIN

As produced in *E. coli*, the gag/env protein is largely confined to cytoplasmic inclusion bodies (insoluble protein aggregates) of the bacterium, a fact which greatly facilitates purification of the protein. To isolate the gag/env protein product of this invention, the bacterial cells are preferably disrupted or lysed and the insoluble protein is recovered by centrifugation. Substantial purification can then be obtained by sequential washing of the precipitate with increasing concentrations of urea followed by the use of standard protein purification techniques.

For small amounts of material such as samples taken for polyacrylamide gel electrophoretic analysis, the cells can be disrupted by treatment with a detergent such as sodium dodecyl sulfate (SDS). Larger quantities of the protein are best recovered by sonication, or by other mechanically disruptive means, such as the French pressure cell.

Cell disruption could also be accomplished by chemical or enzymatic means. Since divalent cations are often required for cell membrane integrity, treatment with appropriate chelating agents such as EDTA or EGTA might prove sufficiently disruptive to facilitate the leakage of the protein from the cells. Similarly, enzymes such as lysozyme have been used to achieve the same result. That enzyme hydrolyzes the peptidoglycan backbone of the cell wall. The application of alternating freezing and thawing in conjunction with lysozyme treatment could also be employed.

Once freed from the cells, the gag/env protein may be identified in the mixture by any of the methods known in the art. For example, a radioimmunoassay or enzyme-linked immunosorbent assay could be carried out using antibodies against the protein. Preferably, the protein is identified by SDS polyacrylamide gel electrophoresis followed by Western blot or similar analysis.

The gag/env protein of the invention can be concentrated by precipitation with salts such as sodium or ammonium sulfate, by ultrafiltration or by the use of other methods well known to those skilled in the art. Further purification can be accomplished by conventional protein purification techniques including but not limited to gel filtration, ion-exchange chromatography, preparative disc-gel or curtain electrophoresis, isoelectric focusing, low temperature organic solvent fractionation or countercurrent distribution.

5.4 USE OF THE GAG/ENV PROTEIN AND ANTIBODIES AGAINST THE PROTEIN

5.4.1. DETECTION OF ANTIBODIES AGAINST AIDS VIRUSES

Because the gag/env protein contains antigenic determinants from two major components of the HTLV-III virus, and because this virus is the principal etiologic agent in AIDS and is immunologically related to the other viral agents which have been implicated in or associataed with AIDS or ARC, the protein is a powerful diagnostic tool for the detection of antibodies against AIDS viruses in human serum. The fusion can be used for this purpose in numerous ways known in the art.

For example, the gag/env protein could be labeled in any number of ways, the labeled protein could be added to a human serum sample suspected to contain antibodies against AIDS viruses to form labeled fusion protein-antibody complexes, and the complexes thus formed could be detected by appropriate means. By way of further example, the protein could be immobilized on a solid support and then contacted with a human serum sample. Antibodies against AIDS viruses in the sample would bind to the immobilized protein, and the complexes thus formed could be detected by the use of a reagent such as *Staphylococcus aureus* protein A (labeled, e.g., with Iodine-125) or a second anti-human IgG antibody (labeled, e.g., with a radioisotope or with horseradish or lactoperoxidase) after uncomplexed proteins and antibodies have been washed away. Many variations on these themes will be apparent to the skilled artisan, some of which are suggested below.

5.4.2. DETECTION OF AIDS VIRUSES OR VIRAL PARTICLES

Through the use antibodies against the gag/env protein, a variety of diagnostic tests for the presence of AIDS viruses or particles therefrom in human serum or in other biological fluids can be devised. Such antibodies can be produced by injecting a mammalian or avian animal with a sufficient amount of a vaccine formulation comprising the protein and a compatible pharmaceutical carrier to elicit the production of antibodies against the protein. The appropriate amount of the protein which would be required would be known to one of skill in the art or could be determined by routine experimentation. As used in connection with this invention, the term "pharmaceutical carrier" can mean either the standard compositions which are suitable for human administration or the typical adjuvants employed in animal vaccinations.

Suitable adjuvants for the vaccination of animals include but are not limited Freund's complete or incomplete adjuvant (not suitable for human or livestock use). Adjuvant 65 (containing peanut oil, mannide monooleate and aluminum monostearate), and mineral gels such as aluminum hydroxide, aluminum phosphate and alum; surfactants such as hexadecylamine, octadecylamine, lysolecithin, dimethyldioctadecylammonium bromide, N,N-dioctadecyl-N'-N'-bis(2-hydroxyethyl)-propanediamine, methoxyhexadecylglycerol, and pluronic polyols; polyanions such as pyran, dextran sulfate, poly IC, polyacrylic acid, carbopol; peptides such as muramyl dipeptide, dimethylglycine, tuftsin; and oil emulsions. The gag/env protein could also be administered following incorporation into liposomes or other microcarriers, or after conjugation to polysaccharides, other proteins or other polymers.

Typically, the initial vaccination is followed some weeks later by one or more "booster" vaccinations, the net effect of which is the production of high titers of antibodies against the gag/env protein, which can be harvested in the usual way.

Of course, monoclonal antibodies against the protein could be produced through current technology to achieve the same result. Somatic cells with the ability to produce antibodies, such as B cells, may be fused with myeloma cell lines to produce hybridoma cells. These cells may be cultured in vitro or as ascites tumors indefinitely to produce large quantities of specific antibodies. Because hybridoma cells may be readily cloned, it is possible to rapidly produce large numbers of cells, all of which produce the same specific antibody molecules directed to a common antigenic determinant. This exceptional uniformity in antibody production may be advantageous where the antibodies are to be used in specific diagnostic tests.

Lymph nodes and spleens of animals of animals primed by injection of an antigen are convenient sources of B cells, although it is equally feasible to remove these cells from unsensitized animals, and to prime them in vitro after isolation. Mouse and rat B lymphocytes are most frequently used in hybridoma production, but cells from rabbits, human beings, frogs or other animals might be used instead.

Numerous specialized myeloma cell lines have been developed from lymphocytic tumors for use in hybridoma production [Kohler and Milstein, European J. Immunol. 6:511 (1976); Shulman et al., Nature 276:269 (1978)]. Of the many such cell lines produced, P3/X63-Ag 8, P3/NSI/1-Ag 4-1, Sp2/0-Ag14, and S194/5.XXO.BU.1 have frequently been used.

The fusion of the antibody-producing spleen or lymph node cells with myeloma cells to produce hybridomas is usually carried out with an excess of splenocytes or lymphocytes over myeloma cells that may be as high as 20:1 although, typically, lower ratios are used. Fusion is facilitated by the use of a fusion-promoting agent such as UV-inactivated Sendai virus or polyethylene glycol (PEG). Gefter et al. [Somatic Cell Genet. 3:231 (1977)] have reported that combining dimethyl sulfoxide with PEG further enhances cell fusion. Electrical devices are also available which can fuse cells with an exceptionally high degree of efficiency.

Once fusion has occurred, the hybridoma cells must be selected from the unfused parental cell strains. This selection process may be readily accomplished by culturing the cells in a medium that supports hybridoma but not parental cell growth. The somatic B cells used in the fusion have limited lifespans in culture and thus will be lost as they undergo senescence and death, but the parental myeloma cells, with indefinite culture lifespans, must be elimintated by special selection techniques.

In a commonly used system, myeloma cells lacking hypoxanthine phosphoribosyl transferase (HPRT$^-$) are used. These cells lack the scavenger pathway for the reutilization of hypoxanthine free base and cannot survive if an inhibitor, such as aminopterin, is used to block the de novo purine synthetic pathways. The myeloma parental cells may thus be selected against by culturing the fusion mixture in hypoxanthine/aminoprotein/-thymidine (HAT) medium, while the hybridoma cells will survive due to the contribution of HPRT by the antibody-producing fusion parental cells.

After a period of selection culturing, the surviving hybridoma cells may be cloned, stocks may be grown up by standard cell culture methods, and clones producing desired specific immunoglobulins may be detected by enzyme-linked immunosorbent assay (ELISA) or by other tests, based upon the use of the antigen against which the antibodies are directed.

The anti-gag/env protein antibodies obtainable through the use of this invention may further be used for the preparation of a variety of diagnostic test for AIDS viruses or particles therefrom. Such diagnostic systems could take the form of a radioimmunoassay, either in free solution or solid state. Alternatively, enzyme-linked immunosorbent assays could be produced, as could assays based on immunoblot analysis. These assays could be direct or indirect, with the application of a second antibody directed against the anti-gag/env protein antibodies. Numerous enzymatic activies could be coupled to the antibodies, with peroxidase, glucose oxidase, $\beta$-galactosidase and alkaline phosphatase being only a few of the possiblities.

The basic principle underlying many of these tests is that a human serum or other biological fluid sample suspected to contain AIDS viruses or fragments therefrom is reacted with a known titer of antibodies against the gag/env protein to form antigen-antibody complexes. The complexes thus formed are detected by an appropriate means.

Those skilled in the art will also recognize that there are many other ways in which anti-gag/env protein antiserum could be utilized in a diagnostic capacity, such as in one of a number of agglutination tests. In such agglutination assays, the interaction of antibodies and AIDS viruses or viral fragments may be detected using systems in which particles are coated with the anti-gag-/env protein antibodies. Such particles may be latex beads, liposomes, erythrocytes, polyacrylamide beads, or any of a number of suitable polymers.

5.4.3. IMMUNIZATION AGAINST AIDS

In copending U.S. patent application Serial No. 725,021, filed Apr. 19, 1985, which is hereby incorporated by reference, it has been stated that the serum of all of 50 AIDS patients tested with genetically engineered env protein was highly reactive to the protein. This was true despite the fact that half of these patients were from the west coast of the United States, and half were from the east coast. The fact that all of the sera tested were reactive to the env protein showed that the viruses producing the antibodies that thus reacted, although geographically separated and undoubtedly somewhat genetically different, must have had at least one common or conserved antigenic determinant in their envelope proteins.

The gag core protein of the AIDS retrovirus has been found to induce antibody formation in a large percentage of individuals who had previously been exposed to the virus. Montagnier et al., in Human T Cell Leukemia/Lymphoma Virus, eds. Gallo et al., Cold Spring Harbor Laboratory, Cold Spring Harbor, N.Y., pp. 363–379 (1984); Schupbach et al., Science 224:503 (1984); Sarngadharan et al., Science 224:505 (1984).

Taken together, the above observations suggest that the gag/env protein of this invention, which has at least one antigenic determinant corresponding to the sequences of the gag and env proteins of which it is comprised, would be immunogenic in human beings and may be useful as an AIDS vaccine.

The gag/env protein (either produced as described herein or chemically synthesized) can be used in a vaccine formulation comprising the protein and a compatible pharmaceutical carrier. The protein can be used as purified in such formulations, or it can be made more immunogenic by modifications known in the art. For example, the protein can be converted into a highly immunogenic matrix by reaction with a cross-linking agent such as 1,3-dicyclohexylcarbodiimide. Alternatively, the protein could be covalently coupled to a highly immunogenic protein carrier molecule, either directly or with an appropriate linker molecule. Carrier molecules which could be used include, e.g., limpet hemocyanin and various bacterial toxoids (inactive toxins) such as diphtheria toxoid. Where the gag/env protein is conjugated to a bacterial toxoid, a bivalent vaccine formulation can be produced that will provide protection against both AIDS and the bacterium from which the toxoid was derived.

Routes of administration, antigen dose, number frequency of injections are all factors falling within the ordinary skill in the art.

6. EXAMPLE

The following is a non-limiting example illustrating the methods by which a recombinant vector encoding the gag/env protein of the HTLV-III virus can be produced. In this example, the following steps were carried out, each of which will be described in detail below:

(1) The DNA sequence encoding residues 15–512 (all but the first 14 amino-terminal residues) of the gag gene was excised from recombinant phage clone λHXB-3 and ligated into E. coli expression plasmid pEV-vrf2 to produce plasmid pEV2/gag 15–512;

(2) DNA sequences corresponding the env amino acid residues 319–331 were deleted from expression plasmid pEV3/env 44–640 by primer-directed mutagenesis to produce plasmid pEV/env 44–640 Δ 319–331;

(3) Primer-directed mutagenesis was carried out on plasmid pEV/env 44–640 Δ 319–331 to produce the deletion of nucleotides encoding amino acid residues 514–524 and plasmid pEV3/env 44–640 Δ 319–331 Δ 514–524; and (4) A restriction endonuclease fragment of the env gene from plasmid pEV/env 44–640 Δ 319–331 Δ 514–524 encoding env residues 467–640 Δ 514–524 was ligated into cleaved plasmid pEV2/gag 15–512, thereby producing a fusion gene encoding gag residues 15–436 and env residues 467–640 Δ 514–524 in plasmid pEV2-/gag 15–436/env 467–640 Δ 514–524.

At each stage of the construction plasmids were reproduced by transformation into E. coli strain MC1061 (pRK248cIts).

6.1. GENERAL PROCEDURES FOR RECOMBINANT VECTOR PREPARATION

6.1.1. DNA PREPARATION

Small scale isolation of plasmid DNA from 1 ml of saturated overnight cultures was carried out according to the procedure of Birnboim et al. [Nucleic Acids Research 7:1513 (1979)]. This procedure allows the isolation of a small quantity of DNA from a bacterial colony for analytical purposes. Larger amounts of plasmid DNA were prepared using 1-liter cultures following a standard protocol with cesium chloride centriguation.

6.1.2. CONDITIONS FOR ENZYMATIC REACTIONS

The restriction enzymes and the T4 DNA ligase used were all products of New England BioLabs, Beverly, MA. The methods and conditions for the use of these enzymes were those published by the manufacturer.

For the restriction endonucleases, a unit of activity is defined as the amount of enzyme needed to produce a complete digest of 1.0 μg DNA in 60 minutes in a total reaction volume of 0.05 ml, with digestion carried out at 376° C. The digestion mixtures, in addition to the DNA to be cleaved, contained 100 μg/ml bovine serum albumin and the following buffer components:

BglII—100 mM NaCl, 10 mM Tris-HCl (pH 7.4), 10 mM MgCl$_2$ and 10 mM 2-mercaptoethanol (2-ME)

ClaI—50 mM NaCl, 6 mM Tris-HCl (pH 7.9) and 6 mM MgCl$_2$

HincII—100 mM NaCl, 10 mM Tris-HCl (pH 7.4), 7 mM MgCl$_2$ and 1 mM dithiothreitol (DTT)

HindIII—50 mM NaCl, 50 mM Tris-HCl (pH 8.0) and 10 mM MgCl$_2$

HpaI—6 mM KCl, 10 mM Tris-HCl (pH 7.4), 10 mM MgCl$_2$ and 1 mM DTT

PstI—100 mM NaCl, 10 mM Tris-HCl (pH 7.5) and 10 mM MgCl$_2$

PvuII—60 mM NaCl, 6 mM Tris-HCl (pH 7.5), 6 mM MgCl$_2$ and 6 mM 2-ME

StuI—100 mM NaCl, 10 mM Tris-HCl (pH 8.0), 10 mM MgCl$_2$ and 6 mM 2-ME

T4 DNA ligation was carried out at 16° C. in a mixture containing the DNA and 50 mM Tris-HCl (pH 7.8), 10 mM MgCl$_2$, 20 mM DTT, 1.0 mM ATP and 50 μg/ml bovine serum albumin. A unit of T4 DNA ligase activity is defined as the amount required to give 50% ligation of HinIII fragments of lambda DNA in 30 minutes at 16° C. in 20 μl of incubation mixture and a 5′ DNA termini concentration of 0.12 μM (300 μg/ml).

6.1.3. PURIFICATON OF DNA FRAGMENTS IN AGAROSE

Following restriction endonuclease cleavage, DNA fragments for cloning were isolated by electrophoresis in 1% agarose. After visualization by 1 μg/ml ethidium bromide, slices of the gel containing desired DNA fragments were extruded through a 21 gauge needle into 4 ml of a solution containing 10 mM Tris-HCl (pH 7.4), 1 mM EDTA and 300 mM NaCl. This mixture was then frozen for 3 hours at 80° C., thawed for 30 minutes at 37° C. and centrifuged at 10,000× for 30 minutes. The supernatant fluid was filtered through a 0.45 micron Millex filter, concentrated to 0.25 ml with sec-butanol and ethanol precipitated three times with 10 μg of E. coli tRNA (transfer RNA) as a carrier.

6.1.4. CULTURE MEDIA

M9CA medium contained 10 g $Na_2HPO_4$, 3 g $KHp_2PO_4$, 0.5 g NaCl and 1 g $NH_4Cl$ per liter, with 1 mM $MgSO_4$, 0.5% glucose and 0.5% casamino acids, adjusted to pH 7.4.

Luria Broth (LB) contained 5 g Bacto-yeast extract, 10 g Bacto-tryptone and 10 g NaCl per liter, adjusted to pH 7.5.

The antibiotics tetracycline and ampicillin were added to final concentrations of 15 and 50 μg/ml, respectively, where indicated.

6.1.5. TRANSFORMATION AND ISOLATION OF RECOMBINANTS

The transformation of E. coli strain MC1061 (pRK248cIts) was carried out using a modification of the protocol of Kushner [in Genetic Engineering, eds. Boyer et al., Elsevier/North-Holland, Amsterdam, p. 17 (1978)], essentially as follows.

Two-hundred ml of the bacterial cells were grown at 30° C. in LB to an $O.D._{600}$ of between 0.5 and 1.0, after which the cells were collected by centrifugation at 6,000× g for 5 minutes at 4° C. and resuspended in 50 ml of a solution containing 10 mM morpholinopropane sulfonic acid (MOPS; pH 7.0) and 10 mM RbCl. The cells were again collected by centrifugation and resuspended in 30 ml of a solution containing 10 mM MOPS (pH 6.5), 50 mM $CaCl_2$ and 10 mM RbCl. After incubation at 0° C. for 30 minutes, the cells were collected, resuspended in 6 ml of 10 mM MOPS (pH 6.5) with 50 mM $CaCl_2$, 10 mM RbCl and 15% glycerol, aliquoted into 40 Eppendorf tubes (300 μl/tube) and frozen at −80° C.

Transformation was performed by thawing a 100 μl aliquot of the cells and incubating for 30, 2 and 2 minutes at 0°, 37° and 0° C., respectively in the presence of a 10 μl sample of ligation mixture containing about 100 ng of DNA and adding 0.1 to 0.5 ml of LB to the tube. The tube was then incubated at 22° C. for 60 minutes, after which 200 μl of the cell suspension were spread onto an LB plate containing ampicillin and incubated at 30° C. for 20 hours.

6.1.6. Cell Growth And Induction Of Gene Expression

Cultures of E. coli MC1061 containing pRK248cIts and an expression plasmid were grown in M9CA medium to mid-log phase at 30° C. and then transferred to 42° C. to inactivate the λ $P_L$ repressor. After a 2 hour incubation at 42° C., cells from 1 ml of the induced culture were collected by centrifugation and resuspended in TG buffer containing pb 10 mM Tris-HCL (pH 7.4) and 10% glycerol in preparation for analysis.

6.1.7. SDS Polyacrylamide Gel Electrophoresis And Western Blot Analysis

Induced cells resuspended in TG buffer were mixed with an equal volume of 2x sample buffer [Laemmli, Nature 227:680 (1970)], incubated at 95° C. for 5 minutes and subjected to SDS polyacrylamide gel electrophoresis in 12.5% gels as described by Laemmli. Following electrophoresis, the proteins from the gel were electroblotted onto a 0.1 micron nitrocellulose membrane for 6 hours at 95 volts in 12.5 mM Tris and 96 mM glycine with 20% methanol and 0.01% SDS at pH 7.5. Western blot analysis was then carried out as described by Towbin et al. [Proc. Natl. Acad. Sci. U.S.A. 76:4350 (1979)].

6.1.8. Primer-Directed Mutagenesis

Primer-directed site specific mutagenesis was performed according to the methods described by Morinaga et al. [Biotechnology 2:636 (1984)]. Synthetic oligonucleotides used to carry out the mutagenesis procedure were prepared by phosphite methodology [Beaucage et al., Tetrahedron Lett. 22:1859 (1981); Matteucci et al., J. Am. Chem. Soc. 103: 3185 (1981)] using an automated synthesizer and purified by polyacrylamide gel electrophoresis by the method of Maxam et al., [Methods in Enzymology 65:499 91980)].

6.1.9. Colony Hybridizations

Colony hydridizations were performed by the method of Grunstein et al. [Proc. Natl. Acad. Sci. U.S.A. 72:3961 (1975)]. The same oligonucleotide used for primer-directed site specific mutagenesis was used as a probe for the hybridizations after 5′ end labeling with $^{32}$P-γ-ATP using polynucleotide kinase as described by Maniatis et al. [Cell 15:687 (1978)].

6.2. Construction Of Plasmid pEV2/GAG 15-512

As noted above, construction of a final expression plasmid expressing the gag/env fusion protein was initiated by construction of a plasmid (pEV2/gag 15-512) containing nucleotides encoding all but the first 14 amino-terminal residues. Some of the nucleotides encoding the carboxyl-terminal gag residues were then replaced by env sequences to obtain the final fusion product.

To make plasmid pEV2/gag 15-512, the DNA sequence encoding residues 15-512 of the gag protein was obtained from 50 μg of recombinant phage lambda clone λHXB-3 containing the HTLV-III proviral genome by cleavage with 50 units of ClaI and 50 units of HincII for 120 minutes at 37° C. to produce a 1700 bp fragemnt. This DNA fragment was isolated by preparative agarose gel electrophoresis and resuspended in 0.1x TE buffer [1mM Tris-HCl (pH 7.4) with 0.1 mM EDTA] to a final concentration of 00.03 pmole/μl.

To receive the gag DNA fragment, 2 μg of the E.coli expression plasmid pEV-vrf2were cleaved with 5 units of ClaI and 5 units of PvuII for 60 minutes at 37°C., and a 1700 bp fragment containing the λ $P_L$ promoter was isolated by electrophoresis in 1% agarose gel and resuspended after ethanol precipitatiion to a final concentration of 0.03 pmole/μl. Plasmid pEV-vrf2 has been described by Crowl et al. [Gene 38:31 (1985] who state that the pEV-vrf vectors are in use in several laboratories and are available upon request.

Three-hundredths pmole of the gag/ClaI-HincII fragment were mixed with 0.03 pmole of the PEV-vrf2/ClaI-PvuII fragment and ligated with 200 units of T4 DNA ligase for 18 hours at 15° C. in a final volume of 10 μl. The ligation product was then transformed into E. coli strain MC1061 (pRK248Its), and transformants were selected by growth on LB agar plates with ampicillin after incubation at 30° C. for 18 hours. The recombinant plasmid DNAs were analyzed for correct restriction fragment size following cleavage with BglII, PstI or HindIII. Isolates positive by DNA size analysis were then evaluated for synthesis of the gag precursor polypeptide by SDS polyacrylamide gel electrophoresis and Western blot analysis.

Cultures harboring plasmid pEV2/gag 15-512 were induced at 40° C., and duplicate samples of the induced cells were prepared for analysis by SDS polyacrylamide gel electrophoresis. After electrophoresis, the gel was bisected, and half of the gel was stained with Coomassie brilliant blue, while the other side of the gel was subjected to electroblotting and Western blot analysis using anti-gag antibodies.

The analysis showed that the induced cells produced proteins which migrated as two major bands in the gels having apparent molecular weights of about 56 and 53 Kd. The size of the complete gag 15-512 protein is about 56 Kd. Both of the major proteins reacted with the anti-gag antibodies. A number of minor lower molecular weight proteins which were reactive with the antibodies were also observed.

Figure 3:
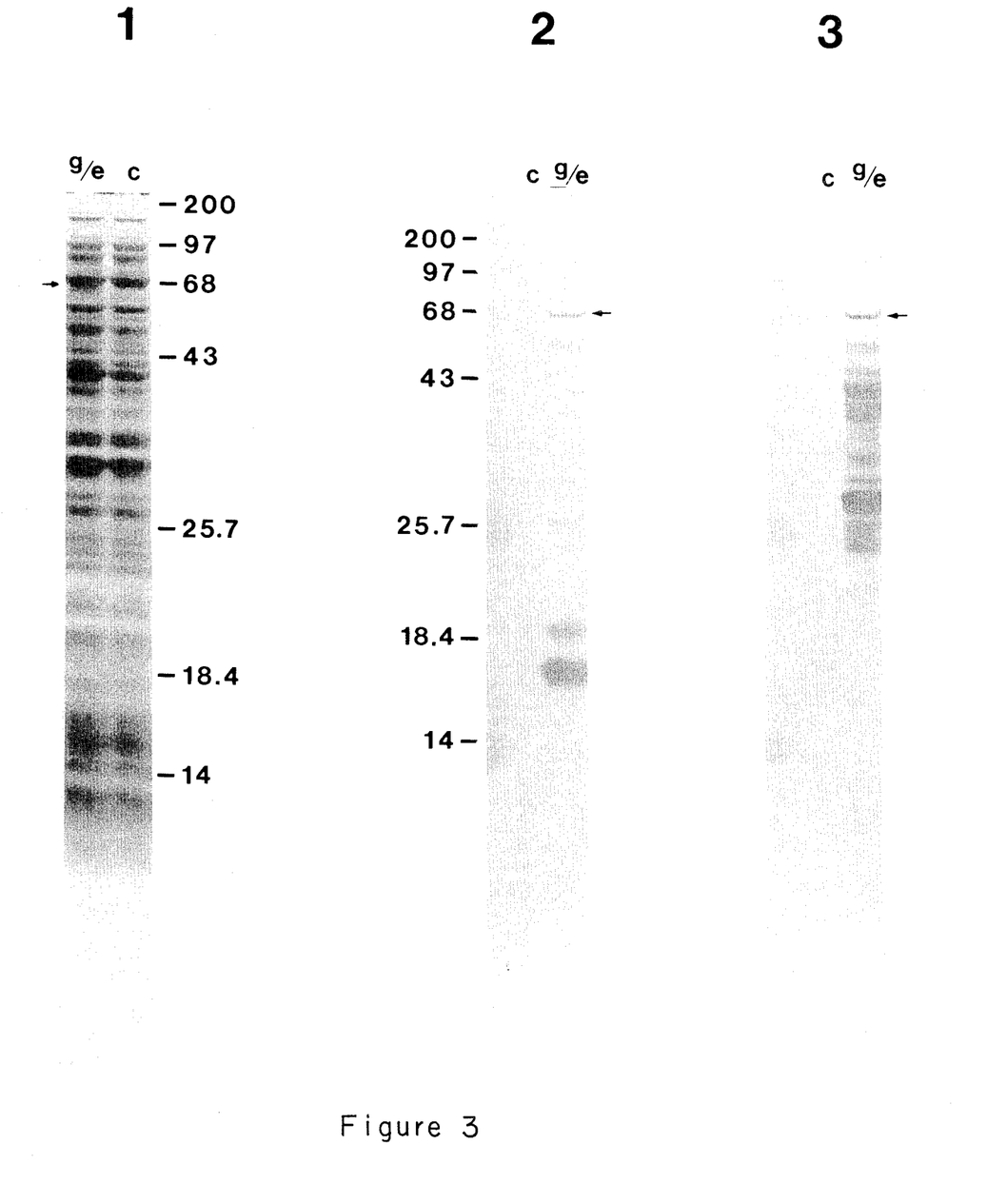

Plasmid pEV-vrf2used in this construction is a derivative of readily available plasmid pBR322. The construction of plasmid pEV-vrf2has been described in detail by Crowl et al. in Gene 38:31 (1985), which is hereby incorporated by reference.

Recombinant phage lambda clone λHXB-3 used in this construction has been described by Shaw et al. [Science 226:1165 (1984)]. This clone was obtained using standard recombinant DNA techniques from the HTLV-III infected H-9 cell line described above. An HTLV-III infected human cell line designated H9/HTLV-IIIB which is suitable for use in this invention has been deposited with the American Type Culture Collection and assigned accession No. CRL8543. Since Shaw et al. have published the sequence of the HTLV-II genome, a DNA probe can easily be constructed using those data which can be used to isolate the genome from H-9 or from any other line capable of propagating the virus.

6.3. Construction Of Plasmid PEV3/ENV 44-640 Δ319-331

The env sequences present in the final exemplary plasmid of this invention were processed in two stages (described in this section and in Section 6.4, below), each of which involved the deletion of specific sort nucleotide sequences by primer-directed site specific mutagenesis. The first of these deletions (described in this section) was required to produce plasmid pEV3-/env 44-640 Δ319-331 Δ514-524 (Section 6.4).

The expression plasmid pEV3/env 44-640, the construction of which from λHXB-3 and the pEV-vf plasmids has been described by Crowl et al. [Cell 41:979 (1985)], directs the synthesis of a 68 Kd HTLV-II env specific protein in *E. coli.* DNA sequences corresponding to env amino acid residues 319-331 were deleted by primer-directed mutagenesis using an 18-mer synthetic oligonucleotide having the sequences 5′ GCA TTT GTT AAC ATT AGT 3′. This oligonucleotide was designed to complement env sequences so as to join nucleotides encoding residue 318 to those encoding residue 332. As a result of bringing these sequences together, a new unique HpaI site was introduced into the plasmid DNA, while 33 bp were deleted. The STuI and HindIII sites in plasmid pEV3/env 44-640 were used to form the "gap" for the heteroduplex molecule.

DNA from isolated colonies which were positive for hybridization to the $^{32}P$-labeled synthetic oligonucleotide during colony screening were transformed into MC1061 (pRK248cITs) and analyzed for the presence of the new, unique HpaI site.

6.4. Construction Of Plasmid pEV3/ENV 44-640 Δ319-331 Δ514-524

A second deletion within the env coding sequences was created by primer directed mutagenesis using a synthetic oligonucleotide having the sequence 5′ AGA GCA GTG GCA GCA GGA 3′. This oligonucleotide positioned sequences encoding residue 513 of the env protein adjacent to those encoding residue 525, thereby facilitating the deletion of the nucleotides encoding residues 514-524. This deletion was produced in the plasmid using the restriction sites HpaI and HindIII to create a single-stranded gap within the env region.

After re-transformation, DNA from positive isolates identified by the $^{32}P$-labeled oligonucleotide probe was analyzed for the 33 bp deletion by restriction cleavage with HpaI and HindIII followed by electrophoresis in 1% agarose. This deletion was also confirmed by DNA sequencing following the chemical cleavage method of Maxam and Gilbert [Methods in Enzymology 65:499 (1980)].

As previously noted, the {514-524 deletion produces a significant increase in the expression of env.

6.5 Construction Of Plasmid pEV2/GAG 15-436/ENV 467-640 Δ514-524

Two μg of pEV2/gag 15-512 were doubly digested with either 5 units of CLAI and 4 units of BGIII to produce about a 1300 bp fragment encoding gag residues 15-436 or with 10 units of PstI and 5 units of ClaI to produce about a 1 Kb fragment containing the λ $P_L$ promoter. Three-tenths μg of pEV3/env 44-640 Δ319-331 Δ514-524 were restricted with 10 units of PstI and 4 units of BgIII to produce about a 4 Kb fragment encoding env residues 467-640 Δ514-524. The various DNA fragments thus produced were separated in 1% agarose and recovered as previously described.

Three-hundredths pmole of each of the isolated DNA fragments were mixed and ligated for 18 hours at 15° C. in the presence of 200 units of t4 DNA ligase. The products of the ligation mixture were then transformed into MC1061 (pRK248cIts), and transformants were selected on LB agar plates with Ampicillin. Plasmid DNA was prepared from unique colonies and analyzed for correct restriction fragment size following digestion with PvuII.

Eleven of 12 isolates were positive by DNA analysis for the expected 3505 and 2882 bp PvuII fragments. Two positive isolates were further evaluated for synthesis of the gag/env fusion protein. These cultures were induced, and cell samples were taken for analysis by SDS polyacrylamide gel electrophoresis, electroblotting and Western blots, with the results shown in FIG. 3.

Panel 1 in FIG. 3 shows Coomassie blue-stained total cell proteins from cells harboring the recombinant plasmid carrying the gag/env fusion gene (g/e) and from control cells (c). Panels 2 and 3 show the results of duplicate samples subjected to Western blot analysis using rabbit polyclonal antibodies against a synthetic peptide corresponding to env residues 500–511 (panel 2) or using sheep polyclonal antibodies against gag protein p24 which is commercially available [panel 3; see Dowbenko et al., Proc. Natl. Acad. Sci. U.S.A. 82:7748 (1985) for description of p24 protein]. In FIG. 3, the immune complexes in panels 2 and 3 were visualized by a second antibody labeled with horseradish peroxidase, and the mobilities of molecular weight standards (in Kd) are indicate. The positions of the gag/env protein bands in the gels are denoted by arrows.

Many modifications and variations of this invention may be made without departing from its spirit and scope, as will become apparent to those skilled in the art. For example, nucleic acid substitutions could be made in the gene coding for the gag/env protein of the invention (using the sequence data contained herein as a reference) and a somewhat different (but functionally equivalent) fusion protein could be produced therefrom. Such an altered product would still be encompassed by this invention as long as it had at least one antigenic determinant corresponding to the sequences of a gag and env protein of an HTLV-III virus. Similarly, the amino acid sequence of the protein itself could be directly manipulate, with the same result. The specific embodiments described herein are offered by way of example only, and the invention is limited only by the terms of the appended claims.

What is claimed is:

1. A protein having the amino acid sequence

10
Met Asn Arg Ile Arg Ile His Arg Trp Glu

20
Lys Ile Arg Leu Arg Pro Gly Gly Lys Lys

30
Lys Tyr Lys Leu Lys His Ile Val Trp Ala

40
Ser Arg Glu Leu Glu Arg Phe Ala Val Asn

50
Pro Gly Leu Leu Glu Thr Ser Glu Gly Cys

60
Arg Gln Ile Leu Gly Gln Leu Gln Pro Ser

70
Leu Gln Thr Gly Ser Glu Glu Leu Arg Ser

80
Leu Tyr Asn Thr Val Ala Thr Leu Tyr Cys

90
Val His Gln Arg Ile Glu Ile Lys Asp Thr

100
Lys Glu Ala Leu Asp Lys Ile Glu Glu Glu

110
Gln Asn Lys Ser Lys Lys Lys Ala Gln Gln

120
Ala Ala Ala Asp Thr Gly His Ser Ser Gln

130
Val Ser Gln Asn Tyr Pro Ile Val Gln Asn

140
Ile Gln Gly Gln Met Val His Gln Ala Ile

150
Ser Pro Arg Thr Leu Asn Ala Trp Val Lys

160
Val Val Glu Glu Lys Ala Phe Ser Pro Glu

170
Val Ile Pro Met Phe Ser Ala Leu Ser Glu

180
Gly Ala Thr Pro Gln Asp Leu Asn Thr Met

190
Leu Asn Thr Val Gly Gly His Gln Ala Ala

200
Met Gln Met Leu Lys Glu Thr Ile Asn Glu

210
Glu Ala Ala Glu Trp Asp Arg Val His Pro

220
Val His Ala Gly Pro Ile Ala Pro Gly Gln

230
Met Arg Glu Pro Arg Gly Ser Asp Ile Ala

240
Gly Thr Thr Ser Thr Leu Gln Glu Gln Ile

250
Gly Trp Met Thr Asn Asn Pro Pro Ile Pro

260
Val Gly Glu Ile Tyr Lys Arg Trp Ile Ile

270
Leu Gly Leu Asn Lys Ile Val Arg Met Tyr

280
Ser Pro Thr Ser Ile Leu Asp Ile Arg Gln

290
Gly Pro Lys Glu Pro Phe Arg Asp Tyr Val

300
Asp Arg Phe Tyr Lys Thr Leu Arg Ala Glu

310
Gln Ala Ser Gln Glu Val Lys Asn Trp Met

320
Thr Glu Thr Leu Leu Val Gln Asn Ala Asn

330
Pro Asp Cys Lys Thr Ile Leu Lys Ala Leu

340
Gly Pro Ala Ala Thr Leu Glu Glu Met Met

350
Thr Ala Cys Gln Gly Val Gly Gly Pro Gly

360
His Lys Ala Arg Val Leu Ala Glu Ala Met

370
Ser Gln Val Thr Asn Thr Ala Thr Ile Met

380
Met Gln Arg Gly Asn Phe Arg Asn Gln Arg

390
Lys Met Val Lys Cys Phe Asn Cys Gly Lys

400
Glu Gly His Thr Ala Arg Asn Cys Arg Ala

-continued

410
Pro Arg Lys Lys Gly Cys Trp Lys Cys Gly

420
Lys Glu Gly His Gln Met Lys Asp Cys Thr

430
Glu Arg Gln Ala Asn Phe Leu Gly Lys Ile

440
Phe Arg Pro Gly Gly Gly Asp Met Arg Asp

450
Asn Trp Arg Ser Glu Leu Tyr Lys Tyr Lys

460
Val Val Lys Ile Glu Pro Leu Gly Val Ala

470
Pro Thr Lys Ala Lys Arg Arg Val Val Gln

480
Arg Gly Lys Arg Ala Val Ala Ala Gly Ser

490
Thr Met Gly Ala Ala Ser Met Thr Leu Thr

500
Val Gln Ala Arg Gln Leu Leu Ser Gly Ile

510
Val Gln Gln Gln Asn Asn Leu Leu Arg Ala

520
Ile Glu Ala Gln Gln His Leu Leu Gln Leu

530
Thr Val Trp Gly Ile Lys Gln Leu Gln Ala

540
Arg Ile Leu Ala Val Glu Arg Tyr Leu Lys

550
Asp Gln Gln Leu Leu Gly Ile Trp Gly Cys

560
Ser Gly Lys Leu Leu Cys Thr Thr Ala Val

570
Pro Trp Asn Ala Ser Trp Ser Asn Lys Ser

580
Leu Glu Gln Ile Trp Asn His Thr Thr Trp

-continued

590
Met Glu Trp Asp Arg Glu Ile Asn Asn Tyr

600
Thr Ser Phe Asn Ala Val Val Tyr His Ser or a sequence related thereto by substitution of one or more amino acids, which protein contains at least one antigenic determinant reactive with antibodies against an AIDS virus corresponding to a sequence of each of a gag and env protein of an HTLV-III virus and its essentially free of other viral proteins.

2. Antibodies against the protein of claim 1.

3. A process for demonstrating the presence of antibodies against an AIDS virus in human serum, comprising:
   (a) reacting a human serum sample suspected to contain antibodies against an AIDS virus with a protein of claim 2 labeled with a detectable label and allowing labeled protein-antibody complexes to form in the reaction mixture; and
   (b) detecting the labeled protein-antibody complexes of step (a),
   thereby demonstrating the presence of antibodies against an AIDS virus in the serum.

4. A process for demonstrating the presence of antibodies against an AIDS virus in human serum, comprising:
   (a) contacting a human serum sample suspected to contain antibodies against an AIDS virus with a protein of claim 1 immobilized on a solid support and allowing immobilized protein-antibody complexes to form;
   (b) washing away unbound protein and antibodies from the complexes of step (a); and
   (c) detecting such complexes by the addition of a reagent selected from the group consisting of labeled Staphylococcus aureus protein A and a labeled second anti-human IgG antibody,
   thereby demonstrating the presence of antibodies against an AIDS virus in the serum.

5. A protein of claim 1 which has been labeled with a detectable label.

6. A protein of claim 1 which has been immobilized on a solid support.

* * * * *